(12) United States Patent
Im et al.

(10) Patent No.: US 9,669,105 B2
(45) Date of Patent: Jun. 6, 2017

(54) LIQUID FORMULATIONS OF LONG-ACTING INTERFERON ALPHA CONJUGATES

(75) Inventors: Dae Seong Im, Yongin-si (KR); Jae Min Lee, Seoul (KR); Jong Soo Lee, Seongnam-si (KR); Sung Min Bae, Seongnam-si (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 0 days.

(21) Appl. No.: 13/881,976

(22) PCT Filed: Oct. 26, 2011

(86) PCT No.: PCT/KR2011/008038
§ 371 (c)(1),
(2), (4) Date: Jul. 2, 2013

(87) PCT Pub. No.: WO2012/057525
PCT Pub. Date: May 3, 2012

(65) Prior Publication Data
US 2013/0287734 A1 Oct. 31, 2013

(30) Foreign Application Priority Data
Oct. 26, 2010 (KR) .................... 10-2010-0104383

(51) Int. Cl.
| *A61K 9/00* | (2006.01) |
| *A61K 38/21* | (2006.01) |
| *A61K 47/26* | (2006.01) |
| *A61K 47/48* | (2006.01) |
| *C07K 14/56* | (2006.01) |
| *C07K 16/46* | (2006.01) |

(52) U.S. Cl.
CPC ...... *A61K 47/48415* (2013.01); *A61K 9/0019* (2013.01); *A61K 38/212* (2013.01); *A61K 47/26* (2013.01); *A61K 47/48369* (2013.01); *A61K 47/48423* (2013.01); *C07K 14/56* (2013.01); *C07K 16/46* (2013.01); *C07K 2319/30* (2013.01)

(58) Field of Classification Search
CPC .... A61K 38/212; A61K 9/0019; A61K 47/26; A61K 47/48369; A61K 47/48415; A61K 47/48423; C07K 16/46; C07K 14/56; C07K 2319/30
See application file for complete search history.

(56) References Cited

U.S. PATENT DOCUMENTS

| 5,762,923 A | 6/1998 | Gross et al. |
| 5,935,566 A * | 8/1999 | Yuen et al. ................. 424/85.7 |
| 2003/0138403 A1 | 7/2003 | Drustrup |
| 2003/0170207 A1 | 9/2003 | Zhang |
| 2005/0002902 A1 | 1/2005 | Yu et al. |
| 2005/0186177 A1 | 8/2005 | Michael et al. |

FOREIGN PATENT DOCUMENTS

| CN | 1141808 A | 2/1997 |
| CN | 1160355 A | 9/1997 |
| CN | 1256148 A | 6/2000 |
| CN | 101217979 A | 7/2008 |
| JP | 2007-528842 A | 10/2007 |
| JP | 2007-536211 A | 12/2007 |
| JP | 2008-505985 A | 2/2008 |
| JP | 2008-50320 A | 3/2008 |
| JP | 2008-545409 A | 12/2008 |
| JP | 2009-525986 A | 7/2009 |
| KR | 10-1999-0085129 A | 12/1999 |
| KR | 10-0567902 B1 | 9/2004 |
| KR | 10-0725315 B1 | 5/2005 |
| TW | i327068 B | 7/2010 |
| WO | 9611018 A1 | 4/1996 |
| WO | 03/020299 A1 | 3/2003 |
| WO | 2004/081053 A1 | 9/2004 |
| WO | 2004/108152 | 12/2004 |
| WO | 2005/047336 A1 | 5/2005 |
| WO | 2006107124 A1 | 10/2006 |
| WO | 2006138181 A2 | 12/2006 |
| WO | 2009015345 A1 | 1/2009 |
| WO | 2010/011096 A2 | 1/2010 |

OTHER PUBLICATIONS

E. Tarelli et al., "Recombinant Human Albumin as a Stabilizer for Biological Materials and for the Preparation of International Reference Reagents", Biologicals, 1998, pp. 331-346, vol. 26.
International Searching Authority, International Search Report of PCT/KR2011/008038 dated May 10, 2012.
Taiwanese Patent Office; Taiwanese Office Action dated Jun. 21, 2013 issued in Taiwanese Application No. 100138828.
State Intellectual Property Office of P.R. China, Communication dated Jun. 20, 2014, issued in corresponding Chinese application No. 201180056378.8.
Japanese Patent Office; Communication dated Jul. 21, 2015 issued in Japanese Application No. 2013-536512.
Russian Patent Office, Communication dated Sep. 14, 2015, issued in corresponding Russian Application No. 2013124059/15.
State Intellectual Property Office of the P.R.C., Communication dated Sep. 11, 2015, issued in corresponding Chinese Application No. 201180056378.8.

(Continued)

*Primary Examiner* — Robert Landsman
*Assistant Examiner* — Bruce D Hissong
(74) *Attorney, Agent, or Firm* — Sughrue Mion, PLLC (57) ABSTRACT

Disclosed is a liquid formulation in which a long-acting INFα conjugate that has improved in vivo duration and stability can be stored stably for a long period of time. It comprises a stabilizer comprising a buffer, a sugar alcohol, a non-ionic surfactant and an isotonic agent. Being free of human serum albumin and other potential factors harmful to the body, the liquid formulation is free of concerns about viral infections and guarantees excellent storage stability to long-acting INFα conjugates.

24 Claims, 1 Drawing Sheet

(56) References Cited

OTHER PUBLICATIONS

Communication issued Jul. 7, 2016 by the Mexican Patent Office in counterpart Mexican Patent Application No. MX/a/2013/004595, with English translation.

* cited by examiner

LIQUID FORMULATIONS OF LONG-ACTING INTERFERON ALPHA CONJUGATES

CROSS REFERENCE TO RELATED APPLICATIONS

This is a National Stage of International Application No. PCT/KR2011/008038 filed Oct. 26, 2011, claiming priority based on Korean Patent Application No. 10-2010-0104383 filed Oct. 26, 2010, the contents of all of which are incorporated herein by reference in their entirety.

TECHNICAL FIELD

The present invention relates to a liquid formulation of long-acting interferon alpha conjugate, comprising a pharmaceutically effective amount of an interferon alpha conjugate, and an albumin-free stabilizer containing a buffer, a sugar alcohol, a non-ionic surfactant and an isotonic agent.

BACKGROUND ART

Interferon was discovered by Isaacs and Lindenmann, who noticed a factor interfering with influenza A virus when a chicken was infected with the virus, in 1957 (Isaacs, K. and Lindenmann, J., Proc. R. Soc. Lond., B147, 258-267 (1957)). Human interferons are proteins known as cytokines that allow communication between cells so that the protective defenses of the immune system that eradicate pathogens such as viruses can be triggered. Depending on the types of cells that release them, interferons are classified into interferon alpha, interferon beta and interferon gamma (Kirchner, H., et al., Tex. Rep. Biol. Med., 41, 89-93 (1981): Stanton, G. J., et al., Tex. Rep. Biol. Med., 41, 84-88 (1981)). That is, interferon alpha is released from B lymphocytes, interferon beta from null lymphocytes and macrophages, and interferon gamma from T lymphocytes with the aid of macrophages. Interferons were reported to exhibit anti-viral activity, anti-cancer activity, the activation of NK (natural killer) cells, and synergistic inhibitory action on mycelocyte growth (Klimpel, et al., J. Immunol., 129, 76-78 (1982); Fleischmann, W. R., et al., J. Natl. Cancer Inst., 65, 863-966 (1980); Weigent., et al., Infec. Immun., 40, 35-38 (1980)). Since then, a large number of studies have discovered that in addition to exhibiting anti-viral effects, interferons act as regulatory factors in the expression, structure and functions of genes within cells, especially direct anti-proliferative effects. Further, a function of interferons is to fight various diseases caused by infections and various tumors.

Interferon alpha is produced in leukocyte cells after exposure to mitogen, viruses or tumor cells. To date, a multigene family of at least 20 genes have been discovered for interferon alpha and are known to encode polypeptides most of which consist of 165 or 166 amino acids.

Clinical tests have demonstrated that recombinant human interferon alpha is effective at treating various solid cancers. Particularly, interferon alpha is known to have effective therapeutic effects on bladder cancer, kidney cancer, and AIDS-associated kaposi's sarcoma (Torti, F. M., J. Clin. Oncol., 6, 476-483 (1988); Vugrin, D., et al., Cancer Treat. Rep., 69, 817-820 (1985); Rios, A., et al., J. Clin. Oncol., 3, 506-512 (1985)). Further, a recent report mentions that interferon alpha is therapeutically applicable to the treatment of hepatitis type C (Davis, G. G., et al., N. Engl. J. Med., 321, 1501-1506 (1989)). Based on these new findings, the therapeutic area of interferon alpha has become wider.

Polypeptides such as interferon alpha tend to easily denature due to their low stability, be degraded by proteolytic enzymes in the blood and to be easily passed through the kidney or liver. Thus, protein drugs, including polypeptides as pharmaceutically effective components, need to be frequently administered to patients to maintain the desired blood level concentrations and titers. However, such frequent administration of protein drugs, most of which are in injection form, causes pain to patients.

To solve these problems, a lot of effort has been put into improving the serum stability of protein drugs and maintaining the drugs in the blood at high levels for a prolonged period of time to maximize the pharmaceutical efficacy of the drugs. For use as long-acting preparations, protein drugs must be formulated to have high stability and have their titers maintained at sufficiently high levels without incurring immune responses in patients.

A conventional approach to stabilizing proteins and preventing enzymatic degradation and clearance by the kidneys is to chemically modify the surface of a protein drug with a polymer having high solubility, such as polyethylene glycol (PEG). By binding to specific or various regions of a target protein, PEG stabilizes the protein and prevents hydrolysis, without causing serious side effects (Sada et al., J. Fermentation Bioengineering 71: 137-139). However, despite its capability to enhance protein stability, PEGylation has problems such as greatly reducing the titers of physiologically active proteins. Further, there is a decrease in the yield with increasing molecular weight of the PEG due to the reduced reactivity of the proteins.

Another alternative strategy for improving the in vivo stability of physiologically active proteins is to link a gene of a physiologically active protein to a gene encoding a protein having high serum stability with the aid of genetic recombination technology and culturing the cells transfected with the recombinant gene to produce a fusion protein. For example, a fusion protein can be prepared by conjugating albumin, a protein known to be the most effective in enhancing protein stability, or its fragment to a physiologically active protein of interest by genetic recombination (PCT Publication Nos. WO 93/15199 and WO 93/15200, European Pat. Publication No. 413,622).

Another method is to use an immunoglobulin as described in U.S. Pat. No. 5,045,312 wherein human growth hormone is conjugated to bovine serum albumin or mouse immunoglobulin by use of a cross-linking agent. The conjugates have enhanced activity, compared with unmodified growth hormone. Carbodiimide or glutaraldehyde is employed as the cross-linking agent. Non-specifically bonding to the peptides, however, such low-molecular weight cross-linking agents do not promise the formation of homogeneous conjugates and are even toxic in vivo. Further, the activity enhancement that the patent is responsible for takes place only because of chemical coupling with the growth hormone. The method of the patent cannot guarantee enhanced activity for various kinds of polypeptide drugs, so that the patent does not recognize even protein stability-related factors, such as duration, the blood half-period, etc.

As such, a long-acting protein drug formulation with improved in vivo duration and stability is required. For use in the long-acting drug formulation, protein conjugates in which a physiologically active polypeptide is covalently linked to a non-polypeptide polymer and an immonoglobulin Fc region have recently been suggested in Korean Patent Nos. 10-0567902 (Physiologically active polypeptide conjugate having improved in vivo durability) and 10-0725315

(Protein complex using an immunoglobulin fragment and method for the preparation thereof).

To apply long-acting interferon alpha conjugates to drug products, it is necessary to maintain the pharmaceutical efficacy thereof in vivo while restraining physicochemical changes such as light-, heat- or additive-induced degeneration, aggregation, adsorption or hydrolysis during storage and transportation. Long-acting interferon alpha conjugates are more difficult to stabilize than interferon alpha polypeptide itself because they are increased in volume and molecular weight.

On the whole, proteins have a very short half life and, when exposed to unsuitable temperatures, water-air interfaces, high pressures, physical/mechanical stress, organic solvents, microbial contamination, etc., they undergo degeneration in the forms of the aggregation of monomers, precipitation by aggregation, and adsorption onto the surface of containers. When degenerated, proteins lose their inherent physicochemical properties and physiological activity. Once degenerated, proteins almost cannot recover their original properties because the degeneration is irreversible. Particularly in the case of proteins administered in a dose of as small as hundreds of micrograms per injection, such as interferon alpha, when they lose stability and thus are absorbed onto the surface of the container, a relatively great amount of damage results. In addition, absorbed proteins easily aggregate during a degeneration process, and aggregates of the degenerated proteins, when administered into the body, act as antigens, unlike proteins synthesized in vivo. Thus, proteins must be administered in a sufficiently stable form.

Many methods have been studied to prevent the degeneration of proteins in solutions (John Geigert, J. Parenteral Sci. Tech., 43(5): 220-224, 1989; David Wong, Pharm. Tech., October, 34-48, 1997; Wei Wang., Int. J. Pharm., 185: 129-188, 1999; Willem Norde, Adv. Colloid Interface Sci., 25: 267-340, 1986; Michelle et. al., Int. J. Pharm. 120: 179-188, 1995).

To achieve the goal of stability, some protein drugs are subjected to lyophilization. However, lyophilized products are inconvenient because they must be re-dissolved in injection water to be used. In addition, they require that a massive investment be made in large-capacity freeze-driers because lyophilization is included in the production process thereof. The contraction of proteins with the use of a spray drier has also been suggested. However, this method is economically unfavorable due to low production yield. Further, a spray-drying process exposes the proteins to high temperature, thus having a negative influence on the stability of the proteins.

As an alternative to overcoming the limitations, stabilizers have appeared that, when added to proteins in solution, can restrain physicochemical changes of protein drugs and maintain in vivo pharmaceutical efficiency even after having been stored for a long period of time. Among these are carbohydrates, amino acids, proteins, surfactants, polymers and salts. Inter alia, human serum albumin has been widely used to stabilize various protein drugs, and its performance in this respect has been verified (Edward Tarelli et al., Biologicals, 26: 331-346).

A typical purification process of human serum albumin includes inactivating biological contaminants such as mycoplasma, prion, bacteria and virus or screening for or examining for the presence of one or more biological contaminants or pathogens. However, there is always the risk of exposing patients to the biological contaminants because they were not completely removed or inactivated. For example, human blood from donors is screened to examine whether it contains certain viruses. However, this process is not always reliable. Particularly, certain viruses existing in a very small number cannot be detected.

Further, different proteins may be gradually inactivated due to the chemical differences thereof because they are subjected to different ratios and conditions during storage. The effect of a stabilizer on the storage term of proteins differs from one protein to another. That is, various stabilizers may be used at different ratios depending on physicochemical properties of the proteins of interest. When concurrently used, different stabilizers may bring about reverse effects due to competition and the erroneous operation thereof. A combination of different stabilizers also elicits different effects because they cause the proteins to change in characteristics or concentration during storage. Because the suitability of the stabilizing activity of each stabilizer is relative to a given range of concentration, care must be exercised when combining different kinds and concentrations of different stabilizers.

Particularly, as pertains to long-acting interferon alpha conjugates which have improved in vivo duration and stability, the molecular weights and volumes thereof are quite different from those of general interferon alpha because they are composed of the physiologically active peptide interferon alpha, non-peptide polymers, and the immunoglobulin fragment Fc. Moreover, the physiologically active peptide interferon alpha and the immunoglobulin fragment Fc must be stabilized simultaneously because both of them are peptides or proteins.

As stated above, different proteins may be gradually inactivated due to the chemical differences thereof because they are subjected to different ratios and conditions during storage. In addition, different stabilizers suitable for respective peptides or proteins, when concurrently used, may incur adverse effects rather than the desired effects, due to competition and the erroneous operation thereof.

Accordingly, it is difficult to establish stabilizer compositions for long-acting interferon alpha conjugates, which are designed to simultaneously stabilize both interferon alpha and an immunoglobulin Fc region.

DISCLOSURE

Technical Problem

Leading to the present invention, intensive and thorough research into the development of a stable liquid formulation for long-acting interferon alpha conjugates, capable of retaining pharmaceutical efficacy for a long period of time without viral infection, resulted in the finding that an albumin-free stabilizer composition comprising a buffer, a sugar alcohol, a non-ionic surfactant and an isotonic agent endows long-acting interferon alpha conjugates with enhanced stability.

Technical Solution

It is therefore an object of the present invention to provide a liquid formulation comprising a pharmaceutically effective amount of a long-acting interferon alpha conjugate in which interferon alpha is covalently linked to an immunoglobulin Fc region, and an albumin-free stabilizer composed of a buffer, a sugar alcohol, a non-ionic surfactant and an isotonic agent.

It is another object of the present invention to provide a method for preparing a liquid formulation of long-acting interferon alpha conjugate, comprising a) constructing a long-acting interferon alpha conjugate; and b) mixing the long-acting interferon alpha conjugate of step a) with an albumin-free stabilizer containing a buffer, a sugar alcohol, a non-ionic surfactant and an isotonic agent.

It is a further object of the present invention to provide a stabilizer for a long-acting interferon alpha conjugate with interferon alpha conjugated with an immunoglobulin Fc region, wherein the stabilizer comprises a buffer, a sugar alcohol, a non-ionic surfactant and an isotonic agent and is free of albumin.

It is still a further object of the present invention to provide a method for stabilizing a long-acting interferon alpha conjugate with a stabilizer, wherein the stabilizer comprises a buffer, a sugar alcohol, a non-ionic surfactant and an isotonic agent and is free of albumin, and the long acting interferon alpha conjugate has interferon alpha covalently linked to an immunoglobulin Fc region.

Advantageous Effects

Being free of human serum albumin and other potential factors harmful to the body, the liquid formulation of long-acting interferon alpha conjugates in accordance with the present invention is freed from concerns about viral infections. Also, the liquid formulation guarantees excellent storage stability to the long-acting interferon alpha conjugates in which interferon alpha and immunoglobulin Fc region are linked and which has larger molecular weight and a longer duration of action than do the natural forms of interferon alpha, thus being economically more beneficial than other stabilizers.

BEST MODE

In accordance with an aspect thereof, the present invention provides a liquid formulation comprising a pharmaceutically effective amount of a long-acting interferon alpha conjugate in which interferon alpha is covalently linked to an immunoglobulin Fc region, and an albumin-free stabilizer composed of a buffer, a sugar alcohol, a non-ionic surfactant and an isotonic agent.

In accordance with another aspect thereof, the present invention provides a stabilizer for a long-acting interferon alpha conjugate with interferon alpha conjugated with an immunoglobulin Fc region, which comprises a buffer, a sugar alcohol, a non-ionic surfactant and an isotonic agent and is free of albumin.

It accordance with a further aspect thereof, the present invention provide a method for stabilizing a long-acting interferon alpha conjugate with a stabilizer, wherein the stabilizer comprises a buffer, a sugar alcohol, a non-ionic surfactant and an isotonic agent and is free of albumin, and the long acting interferon alpha conjugate has interferon alpha covalently linked to an immunoglobulin Fc region.

The term "long-acting interferon alpha conjugate," as used herein may be intended to refer to a protein construct comprising the physiologically active oligopeptide such as interferon alpha (IFNα), at least one non-peptide polymer with a functional group at both ends, and at least one immunoglobulin Fc region, in which the constituents are covalently linked together via covalent bonds.

Thus, the term "long-acting," as used herein, refers to a prolonged duration of action compared to interferon alpha of a natural form. The term "conjugate" refers to a construct in which interferon alpha is covalently linked to the immunoglobulin Fc region by the non-peptide polymer.

The long-acting interferon alpha conjugate is a modified protein drug which is designed to minimize the loss of the inherent physiological activity and to maximally increase in vivo duration. For use in the present invention, the interferon alpha is associated with an immunoglobulin Fc region.

The interferon alpha useful in the present invention may be preferably human interferon alpha. Also, the interferon alpha may be native IFNα, a derivative of native IFNα or a polypeptide having an activity similar to that of native IFNα. That is, the interferon alpha of the present invention may comprise a wild-type interferon alpha amino acid sequence or an amino acid sequence mutant thereof. The term "amino acid sequence mutant," as used herein, refers to an amino acid sequence that is different from the wild-type as a result of deletion, insertion, conserved or non-conserved substitution of one or more amino acid residues, or a combination thereof. The interferon alpha may be native interferon alpha from humans or animals, or may be recombinant interferon alpha from transformed cells. Preferable is recombinant human interferon alpha (HuIFNα) prepared using transformed *E. coli*. Unless their biological activity significantly deviates from that of the wild-type, mutants formed by substitution, deletion or insertion of amino acids are also included within the scope of the interferon alpha.

As used herein, the term "immunoglobulin Fc region" refers to an immunoglobulin fragment that is devoid of the variable regions of light and heavy chains, the constant region 1 of the heavy chain ($C_{H1}$), and the constant region 1 of the light chain ($C_{L1}$), that is, a fragment comprised of the constant regions 2 and 3 of the heavy chain ($C_{H2}$ and $C_{H3}$). Optionally, the immunoglobulin Fc region may further comprise a hinge region. Also, the immunoglobulin Fc region of the present invention may be an extended Fc region which comprises a part of or the entirety of the constant region 1 of the heavy chain ($C_{H1}$) and/or the constant region 1 of the light chain ($C_{L1}$) in addition to the constant regions 2 and 3 of the heavy chain ($C_{H2}$ and $C_{H3}$) so long as it shows effects substantially identical or superior to those of the classical Fc region. Further, the immunoglobulin Fc region of the present invention may be comprised of $C_{H2}$ and/or $C_{H3}$ that lacks a significant part of the amino acid sequence.

Consequently, the immunoglobulin Fc region of the present invention may be composed of 1) $C_{H1}$ domain, $C_{H2}$ domain, $C_{H3}$ domain and $C_{H4}$ domain, 2) CH1 domain and $C_{H2}$ domain, 3) $C_{H1}$ domain and $C_{H3}$ domain, 4) $C_{H2}$ domain and CH3 domain, 5) a combination of one or more constant domains and an immunoglobulin hinge region (or a partial hinge region), or 6) a dimer of each constant domain of the heavy chain and the constant region of the light chain.

Further, an amino acid sequence mutant of the wild-type Fc may be included within the scope of the immunoglobulin Fc region of the present invention. The term "amino acid sequence mutant," as used herein, refers to an amino acid sequence that is different from the wild-type as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification.

Various derivatives, such as those prepared by removing the sites of disulfide bonds, removing several N-terminal amino acids from native Fc, or adding methionine to the N-terminus of native Fc, may be used in the present invention. In addition, complement fixation sites, e.g., C1q fixation sites, or ADCC sites may be eliminated to remove the effector function from the native Fc region. The techniques of preparing amino acid sequence mutants of the immunoglobulin Fc region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. Optionally, amino acids may be modified by phosphorylation, sulfation, acrylation, glycosylation, methylation, farnesylation, acetylation, and amidation.

The above-described Fc derivatives exhibit the same biological activity as that of the wild-type, but are improved in structural stability to heat and pH.

The immunoglobulin Fc region useful in the present invention may be glycosylated to the same extent as or to a higher or lesser extent than the native form or may be deglycosylated or aglycosylated. Increased or decreased glycosylation or deglycosylation of the immunoglobulin region may be achieved by typical methods, for example, by using a chemical method, an enzymatic method, or a genetic engineering method. Herein, when deglycosylated, an immunoglobulin Fc region is significantly decreased in complement (C1q) binding force and has reduced or no antibody-dependent cytotoxicity or complement-dependent cytotoxicity, so that it does not induce unnecessary immune responses in vivo. In this context, deglycosylated or aglycosylated immunoglobulin Fc regions are more consistent with the purpose of drug carriers.

The term "deglycosylation," as used herein, is intended to mean the enzymatic removal of sugars from an Fc region. The term "aglycosylation," when used in conjunction with an Fc region, means an Fc region free of sugars, expressed from prokaryotes, preferably from E. coli.

For use in the present invention, the immunoglobulin Fc region has an amino acid sequence of human immunoglobulin Fc regions or their closely related analogues. The Fc regions may be obtained from native forms isolated from animals including cows, goats, swine, mice, rabbits, hamsters, rats and guinea pigs. In addition, the immunoglobulin Fc region may be an Fc region that is derived from IgG, IgA, IgD, IgE and IgM, or that is made by combinations thereof or hybrids thereof. Preferably, it is derived from IgG or IgM, which is among the proteins that are the most abundant in human blood, and most preferably from IgG, which is known to enhance the serum half-life of the ligand-binding proteins. Herein, the immunoglobulin Fc may be obtained from a native immunoglobulin by isolating whole immunoglobulin from human or animal organisms and treating them with a proteolytic enzyme or it may be recombinants or derivatives thereof, obtained from transformed animal cells or microorganisms. Preferable is recombinant human immunoglobulin Fc produced by E. coli transformants.

The term "combination", as used herein, means that polypeptides encoding single-chain immunoglobulin Fc regions of the same origin are linked to a single-chain polypeptied of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various hybrids are possible. That is, domain hybrids may be composed of one to four domains selected from the group consisting of $C_{H1}$, $C_{H2}$, $C_{H3}$ and $C_{H4}$ of IgG Fc, IgM Fc, IgA Fc, IgE Fc and IgD Fc, and may include hinge region.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc region of IgG4 rarely having an effector function such as CDC (complement dependent cytotoxicity). As the drug carrier of the present invention, the most preferable immunoglobulin Fc region is a human IgG4-derived non-glycosylated Fc region.

The human-derived Fc region is more advantageous than a non-human derived Fc region, which may act as an antigen in the human body and cause undesirable immune responses such as the production of a new antibody against the antigen.

The long-acting interferon alpha conjugate useful in the present invention is prepared by linking the interferon alpha and the immunoglobulin Fc region together. In this regard, the interferon alpha and the immunoglobulin Fc region may be cross-linked via a non-peptide polymer or may be formed into a fusion protein using a recombinant technique.

The long-acting interferon alpha conjugate useful in the present invention may be prepared using a genetic engineering technique, as disclosed in Korean Patent No. 10-0725315.

The non-peptide polymer for use in cross-linking may be selected form the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipid polymers, chitins, hyaluronic acid, and combinations thereof. Most preferred is polyethylene glycol. Also, derivatives thereof well known in the art and able to be easily prepared within the skill of the art are included in the scope of the present invention.

The liquid formation of long-acting interferon alpha conjugate according to the present invention comprises a long-acting interferon alpha conjugate in a pharmaceutically acceptable amount.

The term "pharmaceutically effective amount," as used herein, is intended to refer to a sufficient amount of the pharmaceutical composition to treat a disease, at a reasonable benefit/risk ratio applicable to any medical treatment. The effective amount may vary depending on various factors including the severity and type of the disease being treated, the patient's age and sex, drug activity, sensitivity to drugs, the time of administration, the route of administration, the rate of excretion, the length of the treatment period, the co-administration with other drugs, and other parameters well known in medicinal and pharmaceutical fields. Typically, the pharmaceutically effective amount of interferon alpha ranges from approximately 30 to 200 μg per single-use vial. The concentration of the long-acting interferon alpha conjugates used in the present invention is on the order of 0.1 to 50 mg/ml, and preferably on the order of 0.1 to 5.0 mg/ml.

Particularly, the molecular weights and volumes of long-acting interferon alpha conjugates which have improved in vivo duration and stability are quite different from those of general interferon alpha because they are composed of interferon alpha and the immunoglobulin Fc region. Moreover, the physiologically active peptide interferon alpha and the immunoglobulin fragment Fc must be stabilized simultaneously because both of them are peptides or proteins.

To meet this requirement, a stabilizer is provided in accordance with the present invention. As used herein, the term "stabilizer" is intended to refer to a substance which allows the long-acting interferon alpha conjugate to be safely stored. The term "stabilization" is intended to mean the loss of an active ingredient by up to a predetermined rate, generally, up to 10%, for a certain period of time under a storage condition. When long-acting interferon alpha conjugate retains 90% or more of its original activity and preferably 95% or higher of the original activity after having been stored at 5±3° C. for 2 years, at 25±2° C. for 6 months or at 40±2° C. for one to two weeks, it is understood as being stable.

As for proteins such as the long-acting interferon alpha conjugate, their storage stability is important in suppressing the potential generation of interferon alpha-like antigenic materials as well as guaranteeing that accurate amounts are administered. During storage, about a 10% loss of interferon alpha activity may be understood as being permissible for administration unless the long-acting interferon alpha conjugate within the formulation aggregates or fragments and forms antigenic materials.

The stabilizer suitable for endowing the long-acting interferon alpha conjugate with stability comprises a buffer, a sugar alcohol, an isotonic agent and a non-ionic surfactant, and optionally further methionine.

The buffer in the stabilizer plays a role in keeping the pH of the liquid formulation constant to prevent fluctuations in the pH, thus stabilizing the long-acting interferon alpha conjugate. The buffer useful in the present invention may comprise pharmaceutically acceptable pH buffering agents including alkaline salts (sodium or potassium phosphate, hydrogen or dihydrogen salts thereof), sodium citrate/citric acid, sodium acetate/acetic acid, and a combination thereof.

With reference to the Example section, the stability of the long-acting interferon alpha conjugate varies depending on the pH values of the buffer. The highest stability of the long-acting interferon alpha conjugate was detected at pH 5.5 in citrate buffer (Example 2).

Suitable for use in the present invention is phosphate buffer or citrate buffer, the latter being far more preferred.

The phosphate in the citrate buffer ranges in concentration preferably from 5 to 100 mM and more preferably from 10 to 50 mM.

The buffer has preferably a pH of 4.0 to 7.0, more preferably a pH of 5.0 to 7.0, much more preferably a pH of 5.2 to 7.0, and most preferably a pH of 5.2 to 6.0.

A sugar alcohol is a derivative form of a carbohydrate, whose carbonyl group (=CO) has been reduced to a hydroxyl group (—OH). In the present invention, the sugar alcohol contributes to the stability of the long-acting interferon alpha conjugate.

In the liquid formulation, the sugar alcohol is used preferably at a concentration of from 1 to 10% (w/v), and more preferably at a concentration of 5% (w/v).

The sugar alcohol may be selected from the group consisting of erythritol, galactitol, arabitol, xylitol, sorbitol, ribitol, maltitol, sorbitol, lactitol, and mannitol, with preference for mannitol, sorbitol or a combination thereof.

With reference to the Example section, mannitol was found to contribute the most highly to the stability of the long-acting interferon alpha conjugate under an ordinary buffered solution condition (Example 1).

The isotonic agent acts not only to maintain a suitable osmotic pressure when the long-acting interferon alpha conjugate in the liquid formulation is allowed to enter the body, but to further stabilize the long-acting interferon alpha conjugate in the liquid formation. Examples of the isotonic agent include water-soluble inorganic salts. Preferably representative among them is sodium chloride.

According to an embodiment of the present invention, the use of sodium chloride as an isotonic agent increased the storage stability of the long-acting interferon alpha conjugate in the presence of a buffer, a sugar alcohol and a non-ionic surfactant. From the data, it is understood that sodium chloride as an isotonic agent has a synergistic effect, together with a buffer, a sugar alcohol and a non-ionic surfactant, on the stability of the long-acting interferon alpha conjugate.

Preferably, the concentration of the isotonic agent is on the order of 5 to 200 mM and more preferably on the order of 150 mM. Within this range, the concentration of the isotonic may be adjusted according to the kinds and amounts of the components such that the liquid formulation is isotonic.

Turning now to the non-ionic surfactant, it lowers the surface tension of the protein solution to prevent the proteins from being adsorbed onto or aggregating at hydrophobic surfaces. Polysorbate-type non-ionic surfactants and poloxamer-type non-ionic surfactants are preferably suitable for use in the present invention. They may be used alone or in combination. More preferred are polysorbate-type non-ionic surfactants. Among them are polysorbate 20, polysorbate 40, polysorbate 60 and polysorbate 80, with a greater preference for polysorbate 80.

With reference to the Examples section, a liquid formulation of the long-acting interferon alpha conjugate containing polysorbate 80 was observed to be similar or superior in stability to a liquid formulation containing poloxamer 188. Also, higher stability was detected in a liquid formulation containing 0.02% polysorbate 80 than 0.005% polysorbate 80 (Example 3).

It is not recommended to use the non-ionic surfactant at a high concentration because the non-ionic surfactant, if present at a high concentration, induces interference with protein assays such as UV-spectrometry or iso-focusing to make it difficult to accurately evaluate the concentration or stability of protein.

Thus, the liquid formulation of the present invention may comprise the non-ionic surfactant preferably at a concentration of 0.1% (w/v) or less, more preferably at a concentration of from 0.001 to 0.05% (w/v), and the most preferably at a concentration of 0.02% (w/v).

The stabilizer of the present invention may further comprise methionine. Functioning to prevent the generation of impurities attributed to the oxidation of proteins in a solution, methionine can further stabilize the proteins of interest. Methionine may be preferably used at a concentration of from 0.05 to 0.1% (w/v) based total volume of the formulation and more preferably at a concentration of from 0.01 to 0.1% (w/v).

With reference to the Examples section, the content of oxidized long-acting interferon alpha conjugates in the formulation was found to increase with time in the absence of methionine, but remain relatively constant in the presence of 0.01% methionine, indicating that a liquid formulation containing methionine can further stabilize the long-acting interferon alpha conjugate (Example 5).

In addition, the stabilizer according to the present invention is preferably free of albumin. Because it is prepared from human blood, human serum albumin, available as a stabilizer for proteins, has the possibility of being contaminated by human-derived pathogenic viruses. Gelatin or bovine serum albumin may cause diseases or induce an allergic reaction in some patients. Free of human- or animal-derived serum albumin or heterogeneous proteins such as purified gelatin, there are no concerns about viral infection with the stabilizer according to the present invention.

In addition, the stabilizer of the present invention may further comprise a sugar or a polyhydric alcohol. Preferred examples of the sugar which can be further contained to increase the storage stability of the long-acting interferon alpha conjugate include monosaccharides such as mannose, glucose, fructose and xylose, and polysaccharides such as lactose, maltose, sucrose, raffinose and dextran. Examples of the polyhydric alcohol useful in the present invention include propylene glycol, low-molecular weight polyethylene glycol, glycerol, and low-molecular weight polypropylene glycol. They may be used alone or in combination.

In addition to the above-mentioned components including the buffer, the isotonic agent, the sugar alcohol, the non-ionic surfactant and methionine, the liquid formulation of the present invention may further selectively comprise other components known in the art so long as they do not deteriorate the effect of the present invention.

In accordance with another aspect thereof, the present invention provides a method for preparing a liquid formulation of long-acting interferon alpha conjugate, comprising a) constructing a long-acting interferon alpha conjugate; and b) mixing the long-acting interferon alpha conjugate of step a) with a stabilizer comprising a buffer, a sugar alcohol, a non-ionic surfactant and an isotonic agent.

The above step a) of constructing a long-acting interferon alpha conjugate may be carried out by cross-linking interferon alpha with an immunoglobulin Fc region via a non-peptide polymer or fusing interferon alpha to an immunoglobulin Fc region by means of a recombinant technique.

The cross linking of interferon alpha with an immunoglobulin Fc region via a non-peptide polymer comprises reacting a non-peptidyl polymer having a functional group at each end with interferon alpha and an immunoglobulin Fc region to produce a conjugate in which the non-peptidyl polymer is covalently linked at one end to interferon alpha and at the other end to the immunoglobulin Fc region; and isolating the conjugate.

The covalent bonds among the three components may be formed sequentially or concurrently. For example, when interferon alpha and an immunoglobulin are respectively linked to opposite ends of the non-peptide polymer, either interferon alpha or the immunoglobulin may be first bonded to the non-peptide polymer, followed by bonding the remainder to the polymer. The sequential formation of covalent bonds is advantageous for producing the target conjugate with a minimized number of by-products.

The long-acting interferon alpha conjugate constructed in step a) is mixed with a stabilizer comprising a buffer, a sugar alcohol, a non-ionic surfactant and an isotonic agent to afford the liquid formulation of long-acting interferon alpha conjugate according to the present invention.

Preferably, the stabilizer employs sodium chloride as the isotonic agent, and may further comprise a component consisting of methionine, sugars, polyhydric alcohols, and a combination thereof.

MODE FOR INVENTION

A better understanding of the present invention may be obtained through the following examples which are set forth to illustrate, but are not to be construed as limiting the present invention.

Preparation Example 1

Preparation of Long-Acting Interferon Alpha Conjugate

<1-1> Preparation of Immunoglobulin Fc Region Using Immunoglobulin

To obtain an immunoglobulin Fc region, a solution of 200 mg of 150 kDa immunoglobulin G (IgG, GreenCross, Korea) in 10 mM phosphate buffer was treated with 2 mg of papain (Sigma) at 37° C. for 2 hours with slow stirring. After the enzymatic reaction, the immunoglobulin Fc region thus formed was isolated using column chromatography with a Superdex column, a protein A column, and a cation exchange column. In detail, the reaction was dropwise loaded into a Superdex 200 column (Pharmacia) equilibrated with 10 mM PBS (pH 7.3), followed by eluting with the same buffer at a flow rate of 1 mL/min. Unreacted immunoglobulin (IgG) and F(ab')2 were eluted in advance of the immunoglobulin Fc regions and could be removed because both of them are larger in molecular weight than immunoglobulin Fc regions. Fab, which has a molecular weight similar to that of the immunoglobulin Fc region, was filtered out using Protein A column chromatography. In this context, the fraction of immunoglobulin Fc region eluted from the Superdex 200 column was loaded at a flow rate of 5 mL/min onto a Protein A column (Pharmacia) equilibrated with 20 mM PBS (pH 7.0) and the column was then washed with a sufficient amount of the same buffer to remove unbound proteins. A 100 mM sodium citrate (Na citrate, pH 3.0) buffer was allowed to flow through the column to elute a pure immunoglobulin Fc region. Finally, this Fc fraction eluted from the protein A column was further purified on a cation exchange column (polyCAT, PolyLC) using a linear gradient (NaCl 0.15 M→0.4 M) of 10 mM acetate buffer (pH 4.5).

<1-2> Preparation of IFNα-PEG Complex

ALD-PEG-ALD (Shearwater), a 3.4-kDa polyethylene glycol having an aldehyde reactive group at both ends, was mixed with a 5 mg/mL solution of human interferon alpha-2b (hIFNα-2b, Mw 20 kDa) in 100 mM phosphate buffer at an IFNα:PEG molar ratio of 1:1, 1:2.5, 1:5, 1:10 or 1:20. To this mixture, a reducing agent, sodium cyanoborohydride (NaCNBH$_3$, Sigma), was added in a final concentration of 20 mM and was allowed to react at 4° C. for 3 hrs with gentle agitation. To obtain a 1:1 IFNα-PEG complex in which PEG was selectively linked to the amino end of IFNα, the reaction mixture was subjected to size exclusion chromatography using a Superdex® column (Pharmacia). The IFNα-PEG complex was eluted from the column using 10 mM potassium phosphate buffer (pH 6.0) as an eluent while IFNα not linked to PEG, unreacted PEG, and dimer byproducts where PEG was linked to two IFNα molecules were removed. The purified IFNα-PEG complex was concentrated to 5 mg/ml. Optimal reaction molar ratios of IFNα: PEG which exhibited the most effective reactivity with the minimal production of by-products such as dimers, were identified as ranging from 1:2.5 to 1:5.

<1-3> Construction of IFNα-PEG-Fc Conjugate

The IFNα-PEG complex prepared in <1-2> was linked to the N-terminus of an immunoglobulin Fc region. In this regard, the immunoglobulin Fc region (about 53 kDa) prepared in <1-1> was dissolved in 10 mM phosphate buffer and mixed with the IFNα-PEG complex at an IFNα-PEG complex: Fc molar ratio of 1:1, 1:2, 1:4 or 1:8. After the phosphate buffer concentration of the reaction solution was adjusted to 100 mM, the reducing agent NaCNBH$_3$ was added to the reaction solution at a final concentration of 20 mM and was allowed to react at 4° C. for 20 hrs with gentle agitation. The optimal reaction molar ratio of IFNα-PEG complex:Fc which exhibited the most effective reactivity with the minimal production of by-products such as dimers was identified to be 1:2.

<1-4> Isolation and Purification of IFNα-PEG-Fc Conjugate

After the coupling reaction of <1-3>, Superdex size-exclusion chromatography was performed to remove unreacted substances and byproducts from the reaction mixture to purify the IFNα-PEG-Fc conjugate. The reaction mixture was concentrated and allowed to pass through the column at a flow rate of 2.5 mL/min, together with 10 mM PBS (pH 7.3), to remove unbound Fc and unreacted substance to elute an IFNα-PEG-Fc conjugate fraction. Because a small amount of impurities including unreacted Fc and IFNα dimers also coexisted in the IFNα-PEG-Fc conjugate fraction, cation exchange chromatography was further conducted to remove them. The IFNα-PEG-Fc conjugate fraction was loaded onto a PolyCAT LP column (PolyLC) equilibrated with 10 mM sodium acetate (pH 4.5), followed by eluting with a 10 mM sodium acetate buffer (pH 4.5) containing 1 M NaCl in a linear gradient (NaCl 0 M→0.5 M) manner. Subsequently, an anion exchange column was used to afford a pure IFNα-PEG-Fc conjugate.

This conjugate was further purified using a PolyWAX LP column (PolyLC). The fraction was loaded onto the column equilibrated with 10 mM Tris-HCl (pH 7.5), and eluted with a 10 mM Tris-HCl (pH 7.5) containing 1 M NaCl in a linear gradient (NaCl 0M→0.3 M) manner to produce the IFNα-PEG-Fc conjugate in high purity.

Example 1

Assay of Stability of Long-Acting Interferon Alpha Conjugates According to Various Stabilizers In the presence of phosphate buffer, various stabilizing agents including sugars, sugar alcohols, and amino acids were assayed for their ability to stabilize the long-acting IFNα conjugate.

For the assay, a citrate (Na-citrate) solution (pH 5.5) was used as a buffer, mannitol as a sugar alcohol, arginine or glycine as an amino acid, and sucrose as a sugar.

After storage at 40° C. for one week in the compositions listed in Table 1, RH-HPLC and SE-HPLC analyses were performed. The results are summarized in Table 2, below. In Table 2, RP-HPC (%) and SE-HPLC (%) columns show the retention rate of the long-acting IFNα conjugate compared to the initial value thereof which was expressed as Area % (/Start area %).

TABLE 1

| No. | IFN | Buffer | Stabilizing Agent |
|---|---|---|---|
| 1 | 360 µg/mL | 20 mM Na-Citrate, pH 5.5 | 5% Mannitol |
| 2 | 360 µg/mL | 10 mM Na-Citrate, pH 5.5 | 5% Sucrose |
| 3 | 360 µg/mL | 10 mM Na-Citrate, pH 5.5 | 5% Mannitol 25 mM L-Arginine-HCl |
| 4 | 360 µg/mL | 10 mM Na-Citrate, pH 5.5 | 5% Mannitol 1% Glycine |

TABLE 2

| | RP-HPLC (Area %/Start Area %)% | | SE-HPLC (Area %/Start Area %)% | |
|---|---|---|---|---|
| No. | Week 0 | Week 1 | Week 0 | Week 1 |
| 1 | 100 | 95.3 | 100 | 99.1 |
| 2 | 100 | 92.4 | 100 | 98.5 |
| 3 | 100 | 92.3 | 100 | 98.3 |
| 4 | 100 | 91.8 | 100 | 98.2 |

As is apparent from the data of Table 2, the use of mannitol as a stabilizing agent made the long-acting IFNα conjugate the most stable.

Example 2

Assay of Stability of Long-Acting Interferon Alpha Conjugates According to pH of Stabilizers Stability of the long-acting interferon alpha conjugate was measured in a buffer at various pH values.

After storage at 40° C. for two weeks with the compositions of Table 3 used as the buffer, reverse phase chromatography was performed for the purpose of analysis. For RP-HPLC and SE-HPLC assay, mannitol and polysorbate 80 were used as a stabilizing agent and a surfactant, respectively. The results are summarized in Table 4, below. The retention rate of the long-acting IFNα conjugate compared to the initial value thereof was expressed as Area % (/Start area %) in RP-HPLC (%) and SE-HPLC (%) columns.

TABLE 3

| No. | IFN | Buffer | Isotonic Agent | Stabilizing Agent | Surfactant |
|---|---|---|---|---|---|
| 1 | 360 µg/mL | 20 mM Na-Citrate, pH 5.2 | 150 mM NaCl | 5% Mannitol | 0.005% Polysorbate 80 |
| 2 | 360 µg/mL | 20 mM Na-Citrate, pH 5.5 | 150 mM NaCl | 5% Mannitol | 0.005% Polysorbate 80 |
| 3 | 360 µg/mL | 20 mM Na-Citrate, pH 6.0 | 150 mM NaCl | 5% Mannitol | 0.005% Polysorbate 80 |

TABLE 4

| | RP-HPLC (Area %/Start Area %) % | | | SE-HPLC (Area %/Start Area %) % | | |
|---|---|---|---|---|---|---|
| No. | Week 0 | Week 1 | Week 2 | Week 0 | Week 1 | Week 2 |
| 1 | 100 | Aggregated | Aggregated | 100 | Aggregated | Aggregated |
| 2 | 100 | 95.6 | 91.2 | 100 | 98.5 | 94.4 |
| 3 | 100 | 93.1 | 87.5 | 100 | 93.1 | 87.5 |

As can be seen in Tables 3 and 4, precipitates were formed at a pH of 5.2 after storage for one week and the stability of the long-acting interferon alpha conjugate was enhanced in citrate buffer at pH 5.5, compared to pH 6.0.

From the data, it can be concluded that the long-acting interferon alpha conjugate of the present invention is stabilized to different extents depending on the pH values of buffers used and shows higher stability at some pH values.

Example 3

Assay of Stability of Long-Acting Interferon Alpha Conjugates According to Non-Ionic Surfactant In the presence of citrate buffer, the ability of various non-ionic surfactants to stabilize the long-acting IFNα conjugate was assayed, as follows.

For the assay, polysorbate 80 and Poloxamer 188 were used as the surfactant, and other agents shown to provide stability for the long-acting IFNα conjugate in Example 1, including mannitol, were employed in the proper combination.

Under the same stabilizer condition that IFNα was set to have 360 μg/ml in 20 mM Na-citrate buffer (pH 5.5), the long-acting IFNα conjugate of the present invention was stored at 25±2° C. for four weeks in the compositions listed in Table 5, followed by analysis by RP-HPLC and SE-HPLC. The results are summarized in Table 5, below. The retention rate of the long-acting IFNα conjugate compared to the initial value thereof was expressed as Area % (/Start area %) in RP-HPLC (%). and SE-HPLC (%) columns

TABLE 5

| No. | IFN | Buffer | Surfactant | Sugar Alcohol | Isotonic Agent |
|---|---|---|---|---|---|
| 1 | 360 μg/mL | 20 mM Na-Citrate (pH 5.5) | 0.005% Polysorbate 80 | 5% Manntiol | 150 mM NaCl |
| 2 | 360 μg/mL | 20 mM Na-Citrate (pH 5.5) | 0.02% Polysorbate 80 | 5% Manntiol | 150 mM NaCl |
| 3 | 360 μg/mL | 20 mM Na-Citrate (pH 5.5) | 0.3% Poloxamer 188 | 5% Manntiol | 150 mM NaCl |

TABLE 6

| | | RP-HPLC (Area %/Start Area %) % | | | | SE-HPLC (Area %/Start Area %) % | | | |
|---|---|---|---|---|---|---|---|---|---|
| No. | Surfactant | 0 W | 1 W | 2 W | 4 W | 0 W | 1 W | 2 W | 4 w |
| 1 | 0.005% Polysorbate 80 | 100.0 | 99.6 | 99.2 | 97.1 | 100.0 | 98.9 | 99.9 | 98.7 |
| 2 | 0.02% Polysorbate 80 | 100.0 | 99.8 | 99.6 | 97.7 | 100.0 | 99.2 | 99.8 | 98.7 |
| 3 | 0.3% Poloxamer188 | 100.0 | 99.9 | 99.3 | 97.5 | 100.0 | 100.1 | 100 | 98.7 |

In Tables 5 and 6, the long-acting interferon alpha conjugate only slightly fluctuated in stability irrespective of the types and concentrations of the surfactant, as measured by SE-HPLC, but was found to be the same or higher in stability in polysorbate 80 than in Poloxamer 188 as measured by RP-HPLC. Also, the long-acting interferon alpha conjugate was more stable in a liquid formulation complemented with 0.02% polysorbate 80 than with 0.005% polysorbate 80.

Example 4

Comparison of Storage Stability of Long-Acting IFNα Conjugates Between Inventive Liquid Formulation and Commercially Available Formulation To confirm the stability thereof, the liquid formulation for long-acting interferon alpha conjugate comprising a citrate buffer pH 5.5, NaCl, mannitol and polysorbate 80, all proven in the stability assays of Examples 1 to 3, were compared with a commercially available interferon alpha liquid formulation (INF α2a, Pegasys®).

As shown in Table 7, below, a liquid formulation of long-acting interferon alpha conjugate (liquid formulation #1) was prepared, and the long-acting interferon alpha conjugate was applied to the commercial drug (IFN α2a, Pegasys®) to make a liquid formulation (liquid formulation #2). They were stored at 25±2° C. for two weeks, followed by RP-HPLC analysis. In Table 8, the retention rate of the long-acting interferon alpha conjugate compared to the initial value thereof, is expressed as RP-HPLC (%).

TABLE 7

| No. | IFNα | Buffer | Surfactant | Sugar Alcohol or others | Isotonic Agent |
|---|---|---|---|---|---|
| 1 | 360 μg/mL | 20 mM Na-Citrate (pH 5.5) | 0.02% Polysorbate 80 | 5% Manntiol | 150 mM NaCl |
| 2 | 360 μg/mL | 20 mM Na-Acetate (pH 6.0) | 0.005% Polysorbate 80 | — | 136.9 mM NaCl |

TABLE 8

| | RP-HPLC (Area %/Start Area %)% | | |
|---|---|---|---|
| No. | Week 0 | Week 1 | Week 2 |
| 1 | 100.0 | 99.7 | 99.3 |
| 2 | 100.0 | 99.3 | 98.7 |

As can be seen in the data of Table 8, the liquid formulation in accordance with the present invention can guarantee higher stability to the long-acting interferon alpha conjugate than can the commercially available liquid interferon alpha formulation (IFN α2a, Pegasys®).

Example 5

Assay for Stability of Methionine-Supplemented Liquid Formulation of Long-Acting Interferon Alpha Conjugate To examine the accelerated stability thereof, the liquid formulation, prepared from a stabilizer comprising methionine in addition to citrate buffer (pH 5.5), sodium chloride, mannitol and polysorbate 80, all proven to guarantee the best storage stability in the previous Examples, was stored at 25±2° C. for 4 weeks over which the stability of the long-acting IFNα conjugate was analyzed.

Liquid formulations of the long-acting interferon alpha conjugate were prepared as shown in Table 9, below, and analyzed for stability. In Tables 10 and 11, RP-HPLC (%) and SE-HPLC (%) represent the content of the long-acting interferon alpha conjugate and impurities at each point of time. Results of RP-HPLC and SE-HPLC for accelerated stability assay (25±2° C.) are summarized in Tables 10 and 11, respectively, wherein impurity #6 is an oxidized long-acting interferon alpha conjugate. There was only a small difference in molecular weight between the oxidized and non-oxidized forms of the long-acting interferon alpha conjugate. Thus, SE-HPLC, a method utilizing molecular weights of samples to be analyzed, could not be used to separate the oxidized long-acting interferon alpha conjugate.

TABLE 9

| No. | IFNα | Buffer | Surfactant | Sugar Alcohol and Stabilizing Agent | Isotonic Agent |
|---|---|---|---|---|---|
| 1 | 360 μg/mL | 20 mM Na-Citrate (pH 5.5) | 0.02% Polysorbate 80 | 5% Manntiol | 150 mM NaCl |
| 2 | 360 μg/mL | 20 mM Na-Citrate (pH 5.5) | 0.02% Polysorbate 80 | 5% Manntiol 0.01% Methionine | 150 mM NaCl |

TABLE 10

| | Storage | Content of Conjugate and Impurity (Area %) | | | | | | | | | | |
|---|---|---|---|---|---|---|---|---|---|---|---|---|
| No. | Term | #1 | #2 | #3 | #4 | #5 | #6 | Conjugate | #7 | #8 | #9 | #10 |
| 1 | 0 Week | 0.06 | 0.07 | 0.09 | 0.19 | 0.40 | 1.24 | 96.61 | 0.43 | 0.62 | 0.30 | 0.0 |
|   | 1 Week | 0.09 | 0.06 | 0.28 | 0.19 | 0.41 | 1.62 | 95.85 | 0.56 | 0.63 | 0.31 | 0.0 |
|   | 2 Week | 0.14 | 0.04 | 0.60 | 0.14 | 0.38 | 1.92 | 95.41 | 0.45 | 0.66 | 0.27 | 0.0 |
|   | 4 Week | 0.20 | 0.04 | 0.17 | 0.22 | 0.58 | 1.43 | 93.18 | 0.63 | 0.91 | 0.47 | 0.16 |
| 2 | 0 Week | 0.08 | 0.04 | 0.16 | 0.17 | 0.37 | 1.40 | 96.58 | 0.47 | 0.65 | 0.07 | 0.0 |
|   | 1 Week | 0.12 | 0.07 | 0.46 | 0.23 | 0.40 | 1.28 | 96.14 | 0.58 | 0.51 | 0.20 | 0.0 |
|   | 2 Week | 0.15 | 0.08 | 0.75 | 0.22 | 0.47 | 1.35 | 95.28 | 0.69 | 0.81 | 0.35 | 0.0 |
|   | 4 Week | 0.21 | 0.07 | 0.40 | 0.27 | 0.53 | 1.46 | 94.09 | 0.68 | 0.91 | 0.35 | 0.04 |

TABLE 11

| | Storage | Content of Conjugate and Impurity (Area %) | | | | | |
|---|---|---|---|---|---|---|---|
| No. | Term | #1 | #2 | Conjugate | #3 | #4 | #5 |
| 1 | 0 Week | 0.28 | 0.21 | 99.35 | 0.0 | 0.0 | 0.16 |
|   | 1 Week | 0.48 | 0.0 | 98.92 | 0.0 | 0.38 | 0.22 |
|   | 2 Week | 0.47 | 0.0 | 98.26 | 0.0 | 0.78 | 0.49 |
|   | 4 Week | 0.51 | 0.0 | 96.90 | 1.79 | 0.43 | 0.37 |
| 2 | 0 Week | 0.0 | 0.06 | 99.12 | 0.0 | 0.73 | 0.10 |
|   | 1 Week | 0.0 | 0.13 | 98.59 | 0.0 | 1.07 | 0.22 |
|   | 2 Week | 0.0 | 0.10 | 98.04 | 0.0 | 1.49 | 0.36 |
|   | 4 Week | 0.0 | 0.22 | 96.88 | 0.0 | 1.81 | 1.09 |

As is understood from the accelerated stability assay, the content of an oxidized long-acting interferon alpha conjugate (impurity #6 in RP-HPLC) was increased in the liquid formulation without methionine, but not increased in the liquid formulation supplemented with 0.01% methionine.

These results indicate that methionine endows the long-acting interferon alpha conjugate with additional stability.

Example 6

Figure 1:
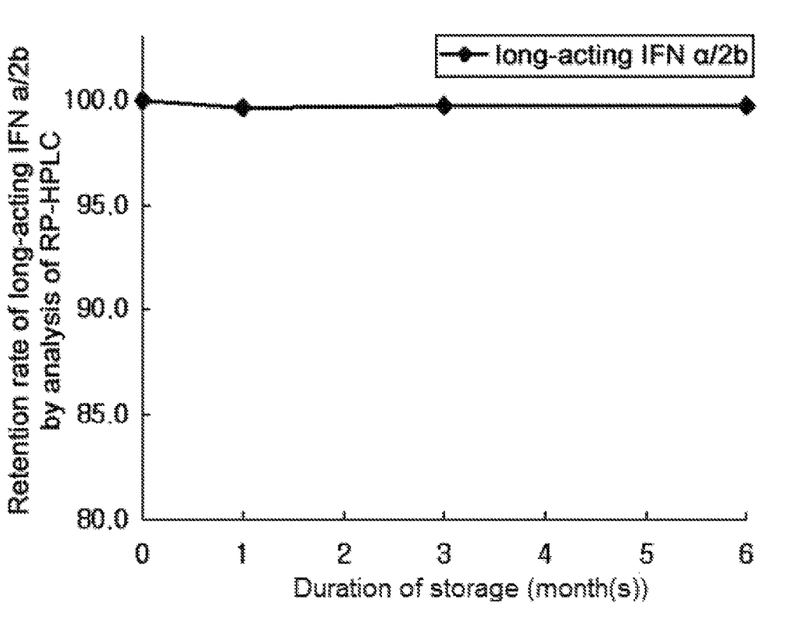
FIG. 1 is a graph showing the stability of the long-acting interferon alpha conjugate in the liquid formulation, pH 5.5, established in Example 6 when it was analyzed using RH-HPLC for the duration of storage at 4° C. for 6 months.

Assay of Liquid Formulation for Long-Term Storage Stability of Long-Acting IFNα Conjugate A liquid formulation containing citrate buffer, pH 5.5, NaCl, mannitol, polysorbate 80 and methionine, all of which had their stabilization activity proven in the previous Examples, was assayed for ability to stabilize the long-acting IFNα conjugate for a long period of time. In this context, the stability of the long-acting IFNα conjugate in the liquid formulation was evaluated after storage at 5±3° C. for six months. The results are shown in FIG. 1 and summarized in Table 12. The retention rate of the long-acting INFα conjugate compared to the initial value thereof was expressed as RP-HPLC (%), SE-HPLC (%), and protein content (%).

TABLE 12

Long-Term Stability Test (Stored at 5 ± 3° C.)

| Storage Term | Property | pH | Confirmation Test | | | Purity Test | | Protein Content Test (%) | Biological Inactivity Test |
| --- | --- | --- | --- | --- | --- | --- | --- | --- | --- |
| | | | RP-HPLC | Western Blot | SDS-PAGE | RP-HPLC (%) | SE-HPLC (%) | | |
| Start | Colorless, Transparent | 5.5 | Coincident | Suitable | Suitable | 100.0 | 100.0 | 100.0 | Suitable |
| Month 1 | Colorless, Transparent | 5.5 | Coincident | Suitable | Suitable | 99.7 | 99.8 | 101.0 | NA |
| Month 3 | Colorless, Transparent | 5.5 | Coincident | Suitable | Suitable | 99.7 | 99.6 | 100.5 | NA |
| Month 6 | Colorless, Transparent | 5.5 | Coincident | Suitable | Suitable | 99.7 | 99.5 | 101.2 | Suitable |

As can be seen in the data, the long-acting interferon alpha conjugate can be stored stably for 6 months or longer in the liquid formulation of the present invention.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. These and other changes can be made to the invention in light of the detailed description.

The invention claimed is:

1. A liquid formulation, comprising
a pharmaceutically effective amount of a long-acting interferon alpha-2 conjugate in which interferon alpha-2 and an immunoglobulin Fc region are covalently linked together via a non-peptide polymer, and
an albumin-free stabilizer consisting essentially of a buffer, a sugar alcohol, a non-ionic surfactant and an isotonic agent, said buffer being a citrate buffered solution or phosphate buffered solution.

2. The liquid formulation of claim 1, wherein the interferon alpha-2 is wild-type interferon alpha-2 or a recombinant interferon alpha-2.

3. The liquid formulation of claim 1, wherein the immunoglobulin Fc region is an Fc region of an immunoglobulin selected from the group consisting of IgG, IgA, IgD, IgE and IgM.

4. The liquid formulation of claim 3, wherein the immunoglobulin Fc region is a hybrid of two or more domains of different isotypes of immunoglobulin, wherein said immunoglobulin is selected from the group consisting of IgG, IgA, IgD, IgE, and IgM.

5. The liquid formulation of claim 3, wherein the immunoglobulin Fc region is a dimer or multimer of plural Fc regions, wherein the plural Fc regions are of a same isotype of immunoglobulin.

6. The liquid formulation of claim 3, wherein the immunoglobulin Fc region is an IgG4 Fc region.

7. The Liquid formulation of claim 6, wherein the immunoglobulin Fc region is an aglycosylated human IgG4 Fc region.

8. The liquid formulation of claim 1, wherein the non-peptide polymer is selected from the group consisting of polyethylene glycol, polypropylene glycol, a copolymer of ethylene glycol and propylene glycol, polyoxyethylated polyol, polyvinyl alcohol, polysaccharide, dextran, polyvinyl ethyl ether, biodegradable polymer, lipid polymer, chitin, hyaluronic acid, and a combination thereof.

9. The liquid formulation of claim 1, wherein the sugar alcohol is selected from the group consisting of mannitol, sorbitol and a combination thereof.

10. The liquid formulation of claim 9, wherein the sugar alcohol ranges in concentration from 1 to 10% (w/v) based on a total volume of the liquid formulation.

11. The liquid formulation of claim 1, wherein the buffer ranges in pH from 4 to 7.

12. The liquid formulation of claim 1, wherein the buffer ranges in pH from 5.2 to 7.

13. The liquid formulation of claim 1, wherein the isotonic agent is sodium chloride.

14. The liquid formulation of claim 13, wherein sodium chloride is at a concentration of from 5 to 200 mM.

15. The liquid formulation of claim 1, wherein the non-ionic surfactant is polysorbate 80.

16. The liquid formulation of claim 15, wherein the non-ionic surfactant ranges in concentration from 0.001 to 0.05% (w/v) based on a total volume of the liquid formulation.

17. The liquid formulation of claim 1, wherein the stabilizer further contains methionine.

18. The liquid formulation of claim 17, wherein methionine ranges in concentration from 0.005 to 0.1% (w/v) based a total volume of the liquid formulation.

19. The liquid formulation of claim 1, wherein the stabilizer further contains a component selected from the group consisting of sugars, polyhydric alcohols and a combination thereof.

20. A liquid formulation, comprising
a pharmaceutically effective amount of a long-acting interferon alpha-2 conjugate in which interferon alpha-2 is covalently linked to an immunoglobulin Fc region through polyethylene glycol, and
a stabilizer consisting essentially of a citrate buffered solution, mannitol, polysorbate 80, sodium chloride and methionine.

21. A method for preparing the liquid formulation of claim 1, comprising:
a) constructing a long-acting interferon alpha-2 conjugate; and
b) mixing the long-acting interferon alpha-2 conjugate constructed in step a) with an albumin-free stabilizer consisting essentially of a buffer, a sugar alcohol, a non-ionic surfactant and an isotonic agent, wherein said buffer is a citrate buffered solution or phosphate buffered solution.

22. The method of claim 21, wherein the isotonic agent is sodium chloride.

23. A stabilizer for stabilizing a long-acting interferon alpha-2 conjugate, wherein the stabilizer consisting essentially of a buffer, a sugar alcohol, a non-ionic surfactant and an isotonic agent and is free of albumin, said long-acting interferon alpha-2 conjugate having interferon alpha-2 covalently linked to an immunoglobulin Fc region,
  wherein said buffer is a citrate buffered solution or phosphate buffered solution.

24. A method for stabilizing a long-acting interferon alpha-2 conjugate with a stabilizer, wherein the stabilizer consisting essentially of a buffer, a sugar alcohol, a non-ionic surfactant and an isotonic agent and is free of albumin, and the long acting interferon alpha-2 conjugate has interferon alpha-2 covalently linked to an immunoglobulin Fc region,
  wherein said buffer is a citrate buffered solution or phosphate buffered solution.

* * * * *